US011135410B2

(12) United States Patent
Finch et al.

(10) Patent No.: US 11,135,410 B2
(45) Date of Patent: Oct. 5, 2021

(54) DEVICES AND METHODS FOR TREATING HEART FAILURE

(71) Applicant: Corvia Medical, Inc., Tewksbury, MA (US)

(72) Inventors: Matthew J. Finch, Medford, MA (US); Edward I. McNamara, Chelmsford, MA (US)

(73) Assignee: Corvia Medical, Inc., Tewksbury, MA (US)

(*) Notice: Subject to any disclaimer, the term of this patent is extended or adjusted under 35 U.S.C. 154(b) by 526 days.

(21) Appl. No.: 15/905,707

(22) Filed: Feb. 26, 2018

(65) Prior Publication Data
US 2018/0256865 A1 Sep. 13, 2018

Related U.S. Application Data

(60) Provisional application No. 62/463,718, filed on Feb. 26, 2017.

(51) Int. Cl.
A61M 27/00 (2006.01)
A61F 2/24 (2006.01)
A61B 17/11 (2006.01)

(52) U.S. Cl.
CPC .......... *A61M 27/002* (2013.01); *A61B 17/11* (2013.01); *A61F 2/2478* (2013.01); *A61B 2017/1107* (2013.01); *A61B 2017/1139* (2013.01); *A61F 2002/249* (2013.01); *A61F 2210/0014* (2013.01); *A61F 2230/005* (2013.01);
(Continued)

(58) Field of Classification Search
CPC .......... A61M 27/002; A61M 2210/125; A61M 2205/0266; A61B 17/11; A61B 2017/1107; A61B 2017/1139; A61F 2/2478; A61F 2210/0014; A61F 2230/0039; A61F 2230/005; A61F 2002/249; A61F 2230/0065; A61F 2205/04
See application file for complete search history.

(56) References Cited

U.S. PATENT DOCUMENTS 8,696,611 B2 * 4/2014 Nitzan .................. A61F 2/2418
604/9
8,926,545 B2 * 1/2015 Brenneman ............ A61B 17/10
604/8
(Continued)

*Primary Examiner* — Julian W Woo
(74) *Attorney, Agent, or Firm* — Helen S Liu

(57) ABSTRACT

The present teachings provide a device to change the pressure in a chamber of a heart and methods of making and using thereof. One aspect of the present teachings provides a device comprising a frame (for example, a metallic frame) and a scaffold. The frame of the device has a distal flange portion, a shunt portion, and a proximal flange portion. The distal and proximal flange portions can align with the shunt portion and form an elongated first profile. At least one of the distal and proximal flange portions can bend radially away from the shunt portion to form a flange like profile. The scaffold includes one or more than covering layers and encloses parts of the frame or the entire frame. The covering layer provides a barrier between the biological matter and the frame of the device. The scaffold is designed to control and direct tissue growth, for example, by stimulating an irritation response and inducing cell proliferation around the retention flange and/or discouraging cell proliferation inside the shunt portion.

14 Claims, 4 Drawing Sheets

(52) U.S. Cl.
CPC ............... *A61F 2230/0039* (2013.01); *A61F 2230/0065* (2013.01); *A61M 2205/0266* (2013.01); *A61M 2205/04* (2013.01); *A61M 2210/125* (2013.01)

(56) References Cited

U.S. PATENT DOCUMENTS

| | | | |
|---|---|---|---|
| 8,940,015 B2* | 1/2015 | Kariniemi | A61B 17/12109 606/213 |
| 10,194,914 B2* | 2/2019 | Mooney | A61B 17/11 |
| 10,363,040 B2* | 7/2019 | Sambandam | A61F 2/06 |
| 10,368,990 B2* | 8/2019 | Noe | A61F 2/2445 |
| 10,470,881 B2* | 11/2019 | Noe | A61F 2/2418 |
| 10,595,999 B2* | 3/2020 | Vettukattil | A61M 27/002 |
| 10,632,292 B2* | 4/2020 | Forcucci | A61F 2/2478 |
| 10,675,450 B2* | 6/2020 | Finch | A61M 27/002 |
| 2004/0143292 A1* | 7/2004 | Marino | A61B 17/0057 606/213 |
| 2009/0187214 A1* | 7/2009 | Amplatz | A61B 17/0057 606/213 |
| 2016/0022970 A1* | 1/2016 | Forcucci | A61F 2/2478 604/8 |
| 2016/0135813 A1* | 5/2016 | Johnson | A61B 17/0057 606/213 |
| 2019/0143011 A1* | 5/2019 | Brenneman | A61B 17/10 604/8 |

\* cited by examiner

DEVICES AND METHODS FOR TREATING HEART FAILURE

FIELD

The present teachings relate to devices and methods of use thereof for treating heart failures. An aspect of the present teachings relates to a device that can be used to change (e.g., reduce) the blood pressure in a heart chamber, for example, by creating a shunt, and optionally regulating the flow of blood through the shunt in order to enhance the therapeutic effect of the shunt. The present teachings further relate to a method of utilizing such a device, for example, in treating congestive heart failure and its related conditions, for example, the acute cardiogenic pulmonary edema caused by an elevated pressure in a left side chamber in the heart.

BACKGROUND

Congestive heart failure (CHF) is a condition that affects millions of people worldwide. CHF results from a weakening or stiffening of the heart muscle that commonly is caused by myocardial ischemia (due to, e.g., myocardial infarction) or cardiomyopathy (e.g., myocarditis, amyloidosis). CHF causes a reduced cardiac output and inadequate blood to meet the needs of body tissues.

Treatments for CHF include: (1) pharmacological treatments, assisting systems, and (3) surgical treatments. Pharmacological treatments, e.g., with diuretics, are used to reduce the work-load of a heart by reducing blood volume and preload. While pharmacological treatments can improve the quality of life, they have little effect on survival. Assisting devices, e.g., mechanical pumps, are used to reduce the load on a heart by performing all or part of the pumping function normally done by the heart. However, in a chronic ischemic heart, high-rate pacings may lead to an increased diastolic pressure, calcium overload, and damages to the muscle fibers. There are at least three surgical procedures for treating a heart failure: (1) heart transplant, (2) dynamic cardiomyoplasty, and (3) the Batista partial left ventriculectomy. These surgical treatments are invasive and have many limitations.

CHF is generally classified into the systolic heart failures (SHF) or the diastolic heart failures (DHF). In a SHF, the pumping action of a heart is reduced or weakened. A normal ejection fraction (EF), the volume of blood ejected out of the left ventricle (stroke volume) divided by the maximum volume remaining in the left ventricle at the end of the diastole or relaxation phase, is greater than 50%. In a systolic heart failure, EF is decreased to less than 50%. A patient with SHF may have an enlarged left ventricle because of cardiac remodeling developed to maintain an adequate stroke-volume. This pathophysiological phenomenon is often associated with an increased atrial pressure and an increased left ventricular filling pressure.

DHF is a heart failure without any major valve disease even though the systolic function of the left ventricle is preserved. Generally, DHF is a failure of the ventricle to adequately relax and expand, resulting in a decrease in the stroke volume of the heart. Presently, there are very few treatment options for patients suffering from DHF. DHF afflicts between 30% and 70% of patients with CHF.

There are several known techniques that can be used to treat the symptoms of DHF. Without attempting to characterize the following references, for example, U.S. Pat. No. 8,091,556 by Keren et al. discloses the use of an interatrial pressure relief shunt with a valve and a tissue affixation element at each end of the shunt; and United States Patent Application Publication No. 20050165344 by Dobak discloses a pressure relief system with an interatrial septal conduit with an emboli barrier or trap mechanism to prevent cryptogenic stroke due to thrombi or emboli crossing the conduit into the left sided circulation. Dobak also discloses a conduit with a one-way valve which directs blood flow from the left atrium to the right atrium.

The constantly evolving nature of heart failures represents a significant challenge for the treatment. Therefore, there is a need for novel and adaptable methods and devices for treating DHF, for example, by creating a pressure relief shunt which can be retrieved, repositioned, adjusted, expanded, contracted, occluded, sealed and/or otherwise altered as required to treat a patient. Furthermore, there exists a need for treating DHF with devices and methods that can self-adjust over time either in accordance with or in anticipation of the gradual hemodynamic changes associated with a heart failure.

SUMMARY

In one aspect, the present teachings relate to a device, having a first elongated profile and a second radially expanded profile, and the device includes a frame and a scaffold, where the scaffold covers at least a portion of the frame. In some embodiments, wherein the frame comprises a first flange portion, a second flange portion, and a shunt portion; the scaffold comprises at least one covering layer. In some embodiments, the first flange portion comprises a plurality of flange segments, the second flange portion comprises a plurality of flange segments, and the shunt portion has a generally tubular shape and comprises a first end and a second end. In some embodiments, the flange segments of the first flange portion position side by side from one another and join the first end of the shunt portion along its entire circumference. In some embodiments, the flange segments of the second flange portion position side by side from one another and join the second end of the shunt portion along its entire circumference. In some embodiments, the covering layer comprises at least one pore. In some embodiments, each of the flange segments of the first and second flange portions aligns parallelly with the longitudinal axis of the shunt portion when the device is in its first elongated profile. In some embodiments, at least one of the flange segments of the first and second flange portions bends radially away from the longitudinal axis of the shunt portion for at least 45° when the device is in its second radially expanded profile. In some embodiments, the pore size of the at least pore maintains substantially the same when the device is in the first elongated profile and the second radially expanded profile.

In some embodiments, the covering layer covers both a portion of the shunt portion and at least one of the first and second flange portion as the device transitions from its first elongated profile to its second radially expanded profile.

In some embodiments, the covering layer covers a bending portion of the device as the devices transitions from its first elongated profile to its second radially expanded profile.

In some embodiments, at least one flange segments of the first flange portion bends radially away from the longitudinal axis of the shunt portion for about 90° as the device transitions from its first elongated profile to its second radially expanded profile.

In some embodiments, at least one flange segments of the second flange portion bends radially away from the longitudinal axis of the shunt portion for about 130° as the device transitions from its first elongated profile to its second radially expanded profile.

In some embodiments, the covering layer is made of a nitinol mesh.

In another aspect, the present teachings relate to a device, having a first elongated profile and a second radially expanded profile, and the device includes a frame and a scaffold. In some embodiments, the scaffold covers at least a portion of the frame. In some embodiments, the frame comprises a first flange portion, a second flange portion, and a shunt portion. In some embodiments, the scaffold comprises at least one covering layer. In some embodiments, the first flange portion comprises a plurality of flange segments. In some embodiments, the second flange portion comprises a plurality of flange segments. In some embodiments, the shunt portion has a generally tubular shape and comprises a first end and a second end. In some embodiments, the frame comprises at least two struts connected with one another. In some embodiments, each of the at least two struts comprises a first end. In some embodiments, the covering layer comprises at least one pore. In some embodiments, two adjacent struts of the at least two struts position next to each other with a first distance between the first ends of the two adjacent struts and the covering layer between the two adjacent struts is folded when the device is in its first elongated profile. In some embodiments, the two adjacent struts move away from each other with a second distance between the first ends of the two adjacent struts and the covering layer extends into a substantially flat surface when the device is in its second radially expanded profile. In some embodiments, the pore size of the at least pore maintains substantially the same when the device is in the first elongated profile and the second radially expanded profile.

In some embodiments, the device in its first elongated profile fits inside a 5 French-12 French catheter.

In some embodiments, the shunt portion expands at least 100% in its diameter when the device changes from the first elongated profile to the second radially expanded profile.

In some embodiments, at least one flange segments of the first and second flange portions bends radially away from the longitudinal axis of the shunt portion for at least 45° as the device transitions from its first elongated profile to its second radially expanded profile.

In some embodiments, the covering layer covers a bending portion of the device as the devices transitions from its first elongated profile to its second radially expanded profile.

In some embodiments, the covering layer is made of a nitinol mesh.

In another aspect, the present teachings relate to a device, having a first elongated profile and a second radially expanded profile. In some embodiments, the device includes a frame and a scaffold, where the scaffold covers at least a portion of the frame. In some embodiments, the frame comprises a first flange portion, a second flange portion, and a shunt portion. In some embodiments, the scaffold comprises a first layer and a second layer. In some embodiments, the first flange portion comprises a plurality of flange segments. In some embodiments, the second flange portion comprises a plurality of flange segments. In some embodiments, the shunt portion has a generally tubular shape and comprises a first end and a second end. In some embodiments, the frame comprises at least two struts connected with one another. In some embodiments, the frame comprises a first side and a second side. In some embodiments, the first layer of the scaffold is disposed against the first side of the frame. In some embodiments, the second layer of the scaffold is disposed against the second side of the frame. In some embodiments, the first and second layers of the scaffold are bond to each other and enclose at least one strut of the frame.

In some embodiments, the flange segments of the first and second flange portions align parallelly to the longitudinal axis of the shunt portion when the device is in its first elongated profile. In some embodiments, at least one of the flange segments of the first and second flange portions bends radially away from the longitudinal axis of the shunt portion for at least 45° when the device is in its second radially expanded profile.

In some embodiments, the scaffold is configured to allow the first and second flange portions move freely without introducing stress to the frame.

In some embodiments, the first layer of the scaffold comprises pores of a first pore size and the second layer of the scaffold comprises pores of a second pore size. In some embodiments, the first and second pore sizes are different. In some embodiments, at least one of the first and second layers of the scaffold is made of multiple members and each of the multiple members comprises pores. In some embodiments, the pores in at least one of the multiple members have different pore size than those in another member. In some embodiments, the pores in the multiple members are of a same size.

DETAILED DESCRIPTION

Figure 1A:
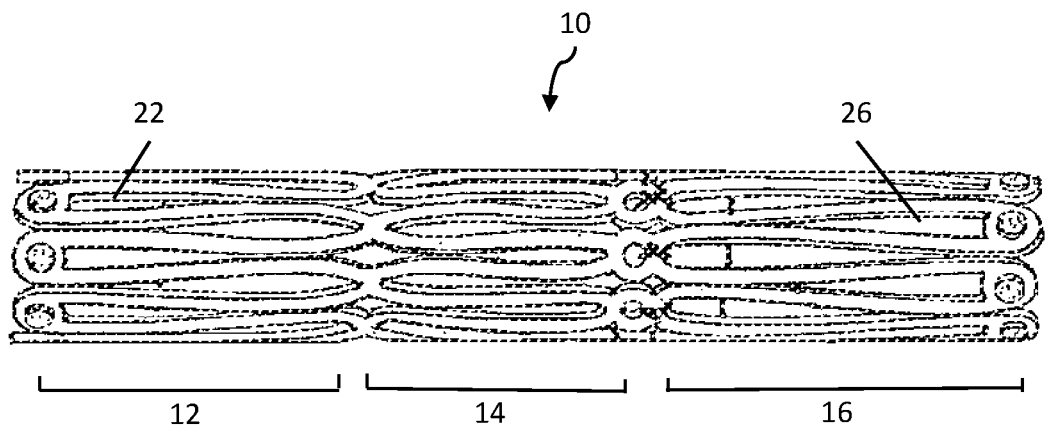
FIG. 1a is a perspective view of an exemplary pressure regulating device in accordance with the present teachings.

The present teachings are described more fully herein with references to the accompanying drawings, which show certain embodiments of the present teachings. The present teachings may, however, be embodied in many different forms and should not be construed as being limited to the embodiments set forth herein. Rather, these embodiments are provided to illustrate various aspects of the present teachings. Like numbers refer to like elements throughout.

The present teachings provide a device and methods of use thereof. For example, the device can be used to regulate the pressure in a heart chamber. Specifically, the device can be used to (a) change an elevated chamber pressure and (b) prevent embolization from the right to left atria in a patient who suffers from CHF or has a patent foramen ovale (PFO)

or an atrial septal defect (ASD) but needs a residual flow between the atria so as not to traumatize the heart hemodynamics.

As used herein, when the terms "distal" and "proximal" are used to refer portion of the device, they can refer to a device in its elongated delivery configuration or its expanded deployed configuration. The term "proximal" shall mean close to the operator (less into the body) and "distal" shall mean remote from the operator (further into the body). In positioning a medical device from a downstream access point, "distal" is more upstream and "proximal" is more downstream.

In some embodiments, when a device of the present teachings is deployed between the two atria, the "distal" side means the left atrial side and the "proximal" side means the left atrial side. In some embodiments, when a device or a part thereof includes a first end and a second end. In some embodiments, the terms "first end" and "second end" do not have any particular orientation and are used merely to differentiate one end from the other. In other embodiments, the terms "first end" and "second end" are used to designate a particular orientation. In some embodiments, the term "first end" means the distal end or the end that resides in and is close to the right atrium and the term "second term" means the proximal end or the end that resides in and is close to the left atrium.

As explained in further detail below, various embodiments of the present teachings provide medical devices for regulating the pressure in a heart chamber. In some embodiments, a medical device according to the present teachings includes a frame and a scaffold. In some embodiments, the frame of the medical device incudes a shunt portion and two flange portions. In some embodiments, the shut portion is coupled with the two flange portions. In some embodiments, the frame of the medical device incudes a radially expandable tubular shunt portion coupled by two radially bendable retention flange portions. In some embodiments, each retention flange portion is configured to bend away from the longitudinal axis of the elongated profile of the frame for at least 45 degrees (45°).

Various embodiments of the present teachings include a first profile and a second profile. That is, in some embodiments, the device includes a first profile and a second profile; and in some embodiments, a part of the device includes a first profile and a second profile. In some embodiments, the first profile is an elongated (or lengthened or straightened) profile and the second profile is an expanded profile. In some embodiments, the expanded profile is a radially expanded profile. In some embodiments, the first profile or the elongated profile is also known as the delivery profile. In some embodiments, the second profile or the radially expanded profile is also known as the deployed profile.

In some embodiments, each retention flange in its elongated profile can have a length equal to twice of the length of the shunt portion. In some embodiments, the scaffold covers at least a portion of the frame. In some embodiments, the scaffold covers the entire frame. In some embodiments, the scaffold allows the physical transformation of the frame through all stages of the implantation. Various embodiments are illustrated and explained herein to facilitate the explanation of the present teachings. One skilled in the art would understand that the principles of the present teachings can be applied to other frame shapes and/or designs. Thus, the scope of present teachings should not be viewed as being limited to these embodiments discussed herein.

Figure 1B:
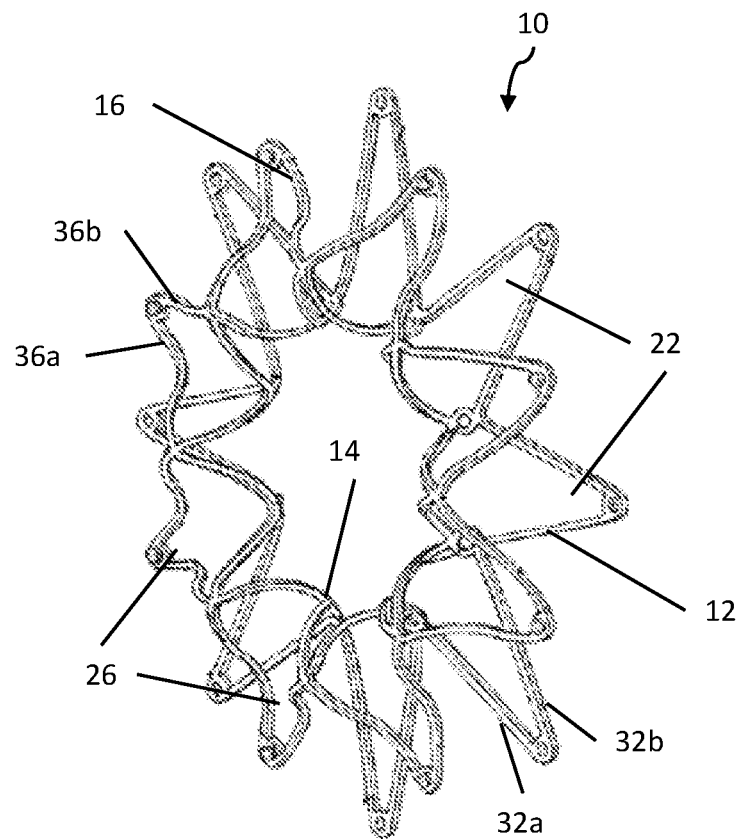
FIGS. 1b-1c are perspective views of an exemplary pressure regulating device of FIG. 1a in accordance with the present teachings.

FIG. 1a illustrates an embodiment of a frame (10) according to one embodiment of the present teachings. As illustrated in FIG. 1a, the frame (10) in its elongated delivery profile has a distal flange portion (12), a shunt portion (14), and a proximal flange portion (16). In some embodiments, the distal flange portion (12), once deployed, forms a distal retention flange portion. In some embodiments, the proximal flange portion (16), once deployed, forms a proximal retention flange portion. In some embodiments, each of the distal flange portion (12) and the proximal flange portion (16) includes a plurality of flange segments (22, 26). All portions of the device is arranged in a longitudinal and generally tubular shape, with the shunt portion collapsing radially and extending longitudinally, and the flange segments (22, 26) of the flanges portions (12, 16) folded inwardly radially. Upon being placed at a treatment site, the shunt portion (14) of the frame (10) expands radially and the flange segments (22, 26) bend radially away from the longitudinal axis of the shunt portion (14). As illustrated in FIG. 1b, the frame (10) in its expanded deployed profile has a shunt portion (14) radially enlarged and/or longitudinally shortened, the distal retention flange segments (22) bending radially outwardly to form a distal retention flange (12), and the proximal retention flange segments (26) bending radially outwardly to form a proximal retention flange (16). As illustrated, each flange segment is formed by two struts (32a, 32b, 36a, 36b) joined at one end and the other ends of the struts (32a, 32b, 36a, 36b) coupled to the shunt portion (14). When the frame (10) is at its delivery profile, the ends of the flange segments (22, 26) come closer to each other. When the frame (10) is deployed, the ends of the flange segments (22, 26) come apart as the shunt portion (14) enlarges radially.

Figure 1C:
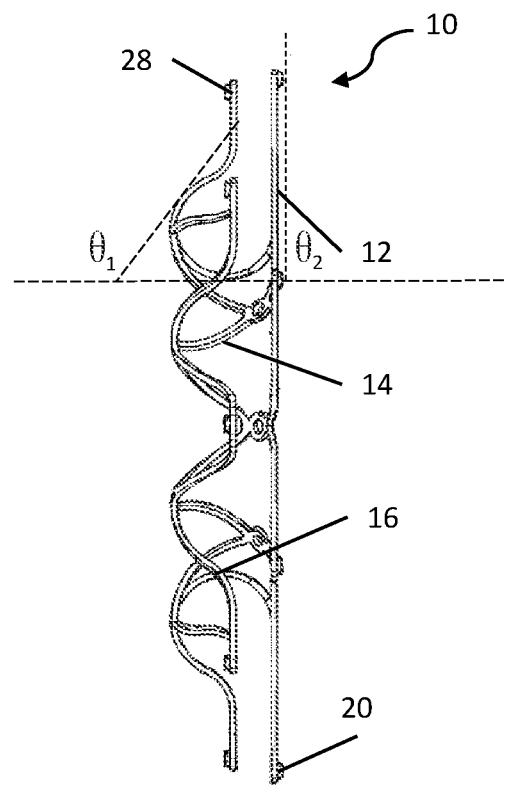

As shown in FIG. 1b, at least one of the distal and proximal flange portions (12, 16) is made of multiple flange segments (22, 26). FIG. 1c illustrates a different view of the expanded frame (10) as shown in FIG. 1b. During the transformation, each flange segment (22, 26) bends radially outwardly. As shown in both FIGS. 1b-1c, the distal flange segments (22) bend away from the longitudinal axis of the shunt portion (14) for approximately 90°, and the proximal flange segments (26) bend away from the longitudinal axis of the shunt portion (14) for about 130°. As further shown in FIGS. 1b-1c, the proximal tip (28) of each the proximal flange segment (26) bend slightly away from the main part of the segment (26). As shown in FIG. 1b, each flange segment (22, 26) comprises two adjacent struts (32a, 32b, 36a, 36b) joined together at one end and the other ends of the struts attached to the shunt portion (14) separately. As the frame transitions from the delivery profile to the deployed profile, as each strut bends away from the longitudinal axis of the shunt potion (14), the two adjacent struts making up a flange segment (32a, 32b, 36a, 36b) bow apart and form a petal-like flange segment. In some embodiments, a frame (10) of the present teachings is designed to be positioned through an aperture across tissues, and create a shunt, for example, between the left and right atria. In some embodiments, the distal and proximal flange portions (12, 16) are disposed on the opposite sides of the septum.

One skilled in the art should understand that what has been illustrated in FIGS. 1a-1c as well as the detailed description therein are merely an exemplary frame design used to assist the explanation of the present teachings. Other frame designs, for example, with similar transformation from one profile to another, could also be incorporated with the scaffold cover without departing from the scope of the present teachings. Examples of the cardiac implant described in conjunction with the drawings of the present teachings have some similarities to those in U.S. Pat. No. 8,043,360, filed on Mar. 8, 2010; U.S. Pat. No. 8,252,042, filed on Mar. 8, 2010; U.S. Pat. No. 8,172,896, filed on Mar. 8, 2010; U.S. Pat. No. 8,157,860, filed on Mar. 8, 2010; and U.S. patent application Ser. No. 12/848,084, filed on Jul. 30, 2010; U.S. patent application Ser. No. 14/645,416, filed on Mar. 11, 2015; U.S. patent application Ser. No. 14/807,544, filed on Jul. 23, 2015; each of which is incorporated by reference herein in its entirety. It, however, should be understood by those ordinarily skilled in the art that other cardiac implants can also be used with embodiments of the present teachings presented herein, such as atrial septal defect occluders, PFO occluders and the like.

In various embodiments, the entire frame is made of a biocompatible metal or polymer. In some embodiments, the frame in its entirety or the portion(s) with curved/bent deployment configuration is made of an elastic material, a super-elastic material, or a shape-memory alloy which allows the above portions to be distorted into a generally straightened profile during the delivery process and resume and maintain its intended profile in vivo once it is deployed, for example, from a delivery catheter. In some embodiments, the frame is made of stainless steel, nitinol, Titanium, Elgiloy, Vitalium, Mobilium, Ticonium, Platinore, Stellite, Tantalum, Platinum, Hastelloy, CoCrNi alloys (e.g., trade name Phynox), MP35N, or CoCrMo alloys, any other metallic alloys, or a mixture thereof. Alternatively, in some embodiments, a part of the frame or the entire frame is made of a polymer, such as PTFE, UHMPE, HDPE, polypropylene, polysulfone, or other biocompatible plastic. In some embodiments, the surface finish of the frame is textured to facilitate better adhesion with the scaffold cover described below.

In some embodiments of the present teachings, the frame of the device is fabricated by laser-cutting or acid-etching a pattern onto a preformed tube thereby forming interconnecting struts with hollowed space in between adjacent struts. In another embodiment, the frame can be formed from wires that are pre-bent into the desired shape and then bonded together to connect elements either by cross-hatching, braiding, welding, or other methods of interconnecting rows of metal that are assembled into a tube-like structure. Other method of fabrication known to those skilled in the art could all be used to fabricate exemplary frame shown herein.

In various embodiments, a method of the present teachings, sometimes referred to as a treatment, starts with a septal puncture which creates an aperture in the atrial septum. A device of the present teachings is then deployed across the aperture. Because the resulting aperture is essentially a fresh wound, the body's natural healing process will start. In some cases, the tissue or cell growth can extend through the openings of the frame and into the tubular opening of the shunt portion of the frame. In some situations, the opening created by the shunt portion of the frame may be blocked or otherwise re-occluded by the tissue growth. Thus, such healing process would then undo all intended treatment over time. Thus, in some embodiments, the entirety or at least a portion of the frame is covered with a biocompatible barrier, for example, to prevent tissue ingrowth.

Figure 2A:
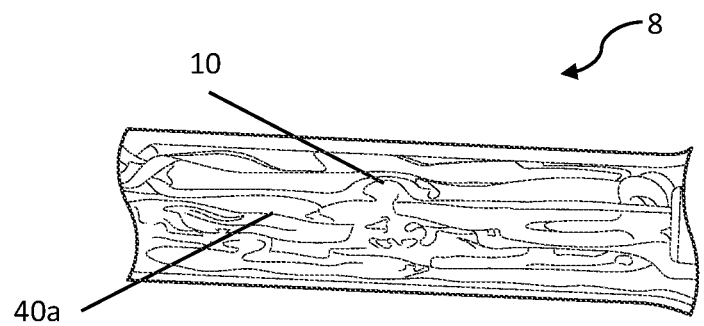
FIG. 2a is another perspective view of an exemplary pressure regulating device where both the distal flange portion, the shunt portion and the proximal flange portion of the device encapsulated with barrier material.
Figure 2B:
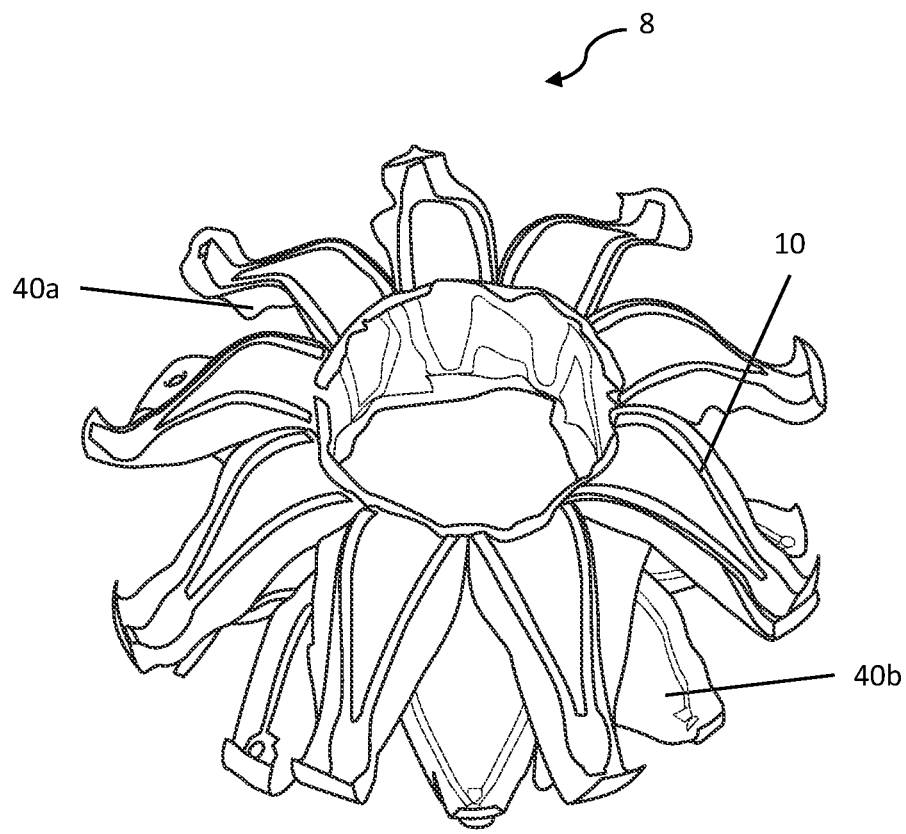
FIG. 2b is perspective view of an exemplary pressure regulating device of FIG. 2a in accordance with the present teachings.

Now referring to and as illustrated in FIGS. 2a-2b, a scaffold of the present teachings attaches to the frame. In some embodiments, the scaffold covers all surfaces of the frame so that no biological matter will be in a direct contact with the device frame. In addition, the scaffold accommodates the movement of the frame during its transition from the delivery profile to the deployed profile. In some embodiments, the scaffold creates a barrier between the biological matter and the metallic frame of the device. The scaffold is designed to control and direct tissue growth by stimulating an irritation response to induce cell proliferation around the retention flange, and/or discourage cell proliferation inside the shunt area.

In some embodiments, as shown in FIG. 2a, where a device (8) of the present teachings is in its elongated delivery profile, a scaffold layer (40a) covers the interior surface of the generally tubular profile of the frame (10). In some embodiments, another scaffold layer covers the exterior surface of the frame. The two layers of the scaffold (40a, 40b) are sealed to each other around every strut that forms the frame of the device. In some embodiments, an enough amount of the scaffold is designed to allow the frame (10) to transform from its delivery profile to an expanded deployed profile, sometimes freely, without introducing any stress to the frame (10). Thus, in a preferred embodiment, two layers of the scaffold is sealed to each other and they enclose a frame in part or entirety at its deployed profile. In some embodiments, as shown in FIG. 2b, at a location where two layers of the scaffold meet each other without a metal strut in between, the two scaffold layers (40a, 40b) are sealed to each other. In some embodiments, as shown in FIG. 2b, at two or more locations (including all) where two layers of the scaffold (40a, 40b) meet each other without a metal strut in between, the two scaffold layers (40a, 40b) are sealed to each other. As shown in FIG. 2b, both ends of the retention flanges are encapsulated inside the scaffold cover.

Figure 3A:
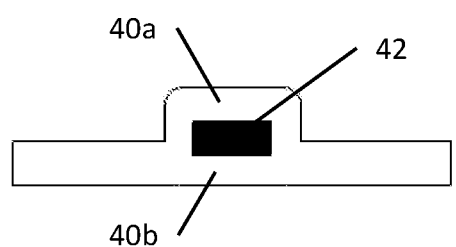
FIG. 3a-3b are perspective cross-section views of exemplary strut of the device being encapsulating between two scaffold layers.
Figure 3B:
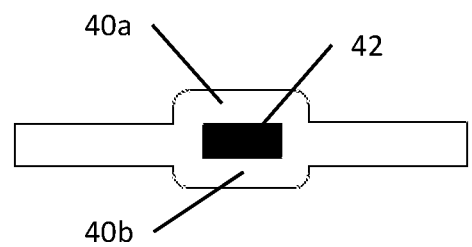

In some embodiments, a degree of control to the smoothness of the device surface is achieved when the scaffold layers (40a, 40b) are being sealed. For example, if a smooth surface is desired, the sealing is biased toward that surface such as illustrated in FIG. 3a, and the other surface is left relatively rough. FIG. 3a illustrates a cross-section view of a strut (42) encapsulated with scaffold layers (40a, 40b), wherein upon bonding two scaffold layers (40a, 40b) together and sealing the strut (42) in between, one surface of remains smooth while the other uneven after bonding. In some embodiments, if a similar smoothness is desired on both sides, the sealing is accomplished somewhere in the middle as illustrated in FIG. 3b. FIG. 3a illustrates a cross-section view of a strut (42) encapsulated with scaffold layers (40a, 40b), wherein upon bonding two scaffold layers (40a, 40b) together and sealing the strut (42) in between, both surface of remains uneven after bonding. In some embodiments, the flange portions (12, 16) of the device (8) comprises a relatively rough surface, for example, to promote tissue growth. In some embodiments, the interior surface of the shunt portion (14) of the device (8) includes a smooth surface, for example, to minimize tissue growth.

In some embodiments, the scaffold material is flexible. In some embodiments, the scaffold material is stretchable. By incorporating a flexible or/and stretchable material, the scaffold layer(s) can accommodate the frame during its transformation from the delivery profile to the deploy profile. In some embodiments, the scaffold material is thin, for example with a thickness around 0.005". By using a thin material, the overall delivery profile of the device can be minimized. In some embodiments, the scaffold material is made of a non-absorbable polymeric material (i.e., a material that does not dissolve after being implanted in the body). Examples of such materials include, without limitation, expanded polytetrafluoroethylene (ePTFE), unexpanded porous PTFE, woven polyester or expanded PTFE yarns, PTFE, ultrahigh molecular weight polyethylene (UHMWPE), other polyolefins, a composite material such as ePTFE with PTFE fibers, or UHMWPE film with embedded UHMWPE fibers, polyimides, silicones, polyurethane, hydrogels, fluoroethylpolypropylene (FEP), polypropylfluorinated amines (PFA), other related fluorinated polymers, metallic materials, polyvinyl alcohol (PVA), extracellular matrix (ECM) isolated from a mammalian tissue, or other bioengineered materials, bioabsorbable polymers, other natural materials (e.g., collagen), nitinol mesh, or various combinations of any of these materials. Furthermore, the surface of the scaffold can be modified with biological, pharmaceutical and/or other active ingredients, such as anti-coagulants, anti-thrombogenic agents, cells, growth factors and/or drugs to diminish calcifications, protein deposition, and thrombus.

Figure 4:
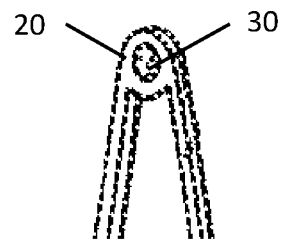
FIG. 4 is a perspective view of a distal tip of the distal flange portion.

In some embodiments, the device (8) is designed to be delivered and deployed percutaneously. In some embodiments, the device (8) is designed to collapse into a tubular profile in order to fit inside a delivery catheter. In some embodiments, the scaffold is designed and configured to accommodate some of these needs. In some embodiments, when a scaffold covered frame collapses into its elongated delivery profile, the scaffold layer between the struts is folded inwardly. In some embodiments, the scaffold layer is tugged inside the tubular profile of the frame (10) as much as possible, for example, to minimize the delivery profile. During a deployment, the device (8) moves distally with respect to the delivery catheter within which the device (8) resides and the delivery catheter therefore slides proximally in relation to the device (8). Such relative movement could cause a proximal pulling effect on the scaffold cover. With the scaffold cover is folded inwardly tugged inside the tubular structure of the frame, the proximal pulling effect can be minimized. In addition, according to some embodiments, the frame (10) could incorporates certain features to prevent the scaffold cover from being sheared off by such proximal pulling force. For example, as illustrated in FIG. 4, the distal tip (20) of the distal flange portion (12) of the frame (10) includes a through hole (30) to allow the scaffold covers (40a, 40b) on both sides of the frame (10) to meet and seal across the hole (30). Such sealing assists the scaffold layers (40a, 40b) to resist from the proximal pull during the deployment of the device (8). Holes with various configurations and dimensions can be incorporated into the frame (10) at various portions, including the shunt portion (14), and/or the proximal flange portion (16). One ordinarily skilled in the art would also understand that other features can also be used to prevent scaffold cover from being torn by the proximal shearing force during the device deployment. The embodiments shown and described herein should not be viewed as attempts to limit the scope of the present teachings.

One ordinarily skilled in the art would understand that the scaffold layers (40a, 40b) must be bonded to the frame (10) to prevent it from detaching and perhaps forming emboli in the heart. In some embodiments, the material used as a barrier can be difficult to be attached to a metallic frame (10). Mechanical fasteners such as sutures might have the disadvantage of interrupting the integrity of the scaffold layers material so that leaks may occur. Thus, for a material that does not adhere well to a metallic frame, it can be made to bond to itself. For example, one method of affixing the ePTFE cover is to place ePTFE covers in contact with both the abluminal and luminal surfaces of the shunt portion of the device so that one ePTFE covering can bond to the other where the ePTFE coverings come to contact through the openings in the shunt portion. In some embodiments, the pieces and/or layers of the scaffold are bonded by a number of methods, including sintering (i.e., heating), suturing, ultrasonic welding, stapling, or adhesive bonding. In a preferred embodiment, the device is subjected to heat and pressure to bond the scaffold layers together.

According to some embodiments, each layer of the scaffold is made of a continue piece of material. In some embodiments, the scaffold is made of a material with consistent character and pore size. One ordinarily skilled in the art would understand that each layer of the scaffold can include multiple scaffold pieces for ease of manufacturing. For example, two disc-shaped scaffolds can be used to cover the two flange portions (12, 16), a tubular-shaped scaffold piece used to cover the shunt portion of the frame (10). In some embodiments, the three pieces of scaffolds are sealed to one another to make a complete layer. When the layer includes two or more pieces, each of the pieces can have a same pore size or different pore sizes. For example, the scaffold piece covering the flange portions (12, 16) can have pores of a first pore size, and the scaffold piece covering the shunt portion (14) can have pores of a second pore size. In some embodiments, the first pore size is greater than the second pore size. By using pores of different pore sizes, cell proliferation and/or tissue growth can be facilitated, encouraged, lessened, limited, or prevented. In another embodiment, when the scaffold layer includes two or more pieces, the pieces can be made of different materials, for example, each with different tissue growth character. In some embodiments, all scaffold materials are compatible to one another. In some embodiments, all scaffold materials can be sealed to one another. In some embodiments, pore sizes of the scaffold layer are distorted during the bonding process. In some embodiments, a post bonding process is incorporated to puncture additional holes to the cover material. In some embodiments, the additional pores are prepared by using laser or other methods generally known to those ordinarily skilled in the art.

According to some embodiments, the final pore size of the scaffold layer bonded to the frame (10) vary from 4 to 110 microns. In some embodiments, the average pore size of the final pores ranges from 9 to 65 microns. In some embodiments, the thickness of the scaffold layer varies from 0.3 to 0.75 mm. In some embodiments, the density of the scaffold layer ranges from 0.24 to 0.35 g/ml. According to some embodiments, the pore size of the scaffold layer is the primary determinant of tissue ingrowth. Thus, one ordinarily skilled in the art would understand that the tissue ingrowth to the device, once deployed in vivo, can be controlled by a clinician by choosing and manufacturing material with appropriate pore sizes.

Figure 5:
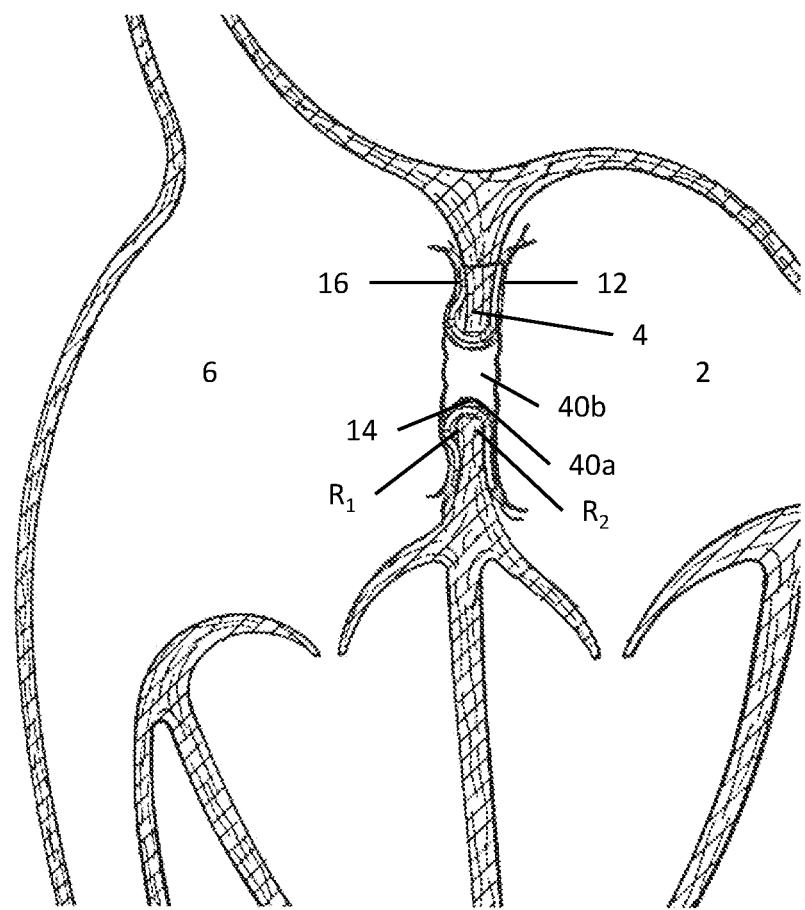
FIG. 5 illustrates a perspective view of an exemplary pressure regulating device being positioned through an aperture between the left and right atria.

FIG. 5 illustrates certain embodiments of the present teachings where an embodiment of the device (8) is deployed across the atrial septum. In some embodiments, the device (8) is deployed with the distal flange segments (22) deployed inside the left atrium (2), the shunt portion (14) positioned across an aperture on the atrial septum (4), and the proximal flange segments (26) deployed inside the right atrium (6). According to one embodiment of the present teachings, upon deployment, the stiff shunt portion (14) pushes the surrounding tissue radially outwardly and maintain the size of the opening of the treatment, and the relative pliable proximal and distal flange portions (12, 16) gently contact the septal tissue without penetration. Also as shown in FIG. 5, each of the left and proximal flange segments (22, 26) is covered with a first scaffold layer and a second scaffold layer of scaffold (40a, 40b). The first scaffold layer (40a) contacts or is in close proximity to the atrial septum (4), and the second scaffold layer (40b) is exposed to the blood inside the heart. The shunt portion (14) of the device (8) is also covered with an inner luminal scaffold layer (40b)

and an exterior scaffold layer (40a). The exterior luminal scaffold layer (40a) is in contact with the atrial septal tissue (4) and the interior scaffold layer (40b) is exposed to the blood inside the heart.

According to some embodiments, the distal flange portion (12) forms a disc-like configuration, with a substantial portion of the surface area of each flange segment (22) contacting the atrial septum. As shown in FIG. 5, the distal flange segments (22) bends at the angle of "$\theta_1$" from its delivery profile, such as those shown in FIG. 1c. One ordinarily skilled in the art would understand that although what is shown in FIG. 5 is a disc-like distal flange portion (12) with a bending angle at approximately 90°, other suitable profiles, such as an umbrella shaped left flange profile, can also be used. As the contact area between the left flange segment (22) and atrial septum (4) varies, the degree of tissue ingrowth on the first scaffold layer (40a) can also vary. In some embodiments, by controlling the degree of contract between the flange segments (22) and the septal tissue (4), the degree of tissue ingrowth can be controlled.

According to some embodiments, the shunt portion (14) has a longitudinal length similar or longer than the thickness of an atrial septum (4). As shown in FIG. 5, with the disc-like deployed distal flange (22) positioned against the left side of the atrial septum (4), the proximal end of the shunt portion (14) is then extended inside the right atrium (6). Continuing referring to FIG. 5, the proximal flange portion (16) deploys inside the right atrium (6) and each of the flange segments (26) bends toward the right side of the atrial septum (4) at the angle of "$\theta_2$" from its delivery profile as shown in FIG. 1c. The free ends of the proximal flange segments (26) contact the septal tissue with the substantial area of the proximal flange segments (26) disposed within the proximity of the septal tissue (4). As shown in FIG. 5, a small space remains between the septal tissue (4) and the first scaffold layer (40a) of the proximal flange segments (26). One ordinarily skilled in the art would understand, the embodiments shown here are designed to accommodate various thicknesses of the atrial septum (4). For example, the thicker is the atrial septum, the less is the bending angle "$\theta_2$"; and the thinner is the atrial septum, the greater is the bending angle "$\theta_2$". In some embodiments, the bending angle "$\theta_2$" ranges from 90° to 180°. Similarly, the contacting area between the proximal flange segments (26) and the atrial septum (4) can vary, and the degree of tissue ingrowth can also vary from a patient to another.

FIG. 5 further illustrates that, upon deployment, two generally curved sections, $R_1$ and $R_2$, are formed, including one at a distal portion of the shunt portion (14) and an adjacent portion of the distal flange segments (22) and the other at a proximal portion of the shunt portion (14) and an adjacent portion of the proximal flange segments (26). According to one embodiment of the present teachings, the device is pre-set into its deployed profile and stretched into an elongated profile, such as those shown in FIGS. 1a and 1b, for the percutaneous delivery. Upon deployment and free from the constraint of the delivery catheter, the device (8) recovers to its pre-set deployed configuration. According to some embodiments, each of the scaffold layers (40a, 40b) on the distal flange segments (22), the proximal flange segments (26), and the shunt portion (14) of the devices (8) also transitions with the frame (10) of the device (8) without any substantial distortion to its original pore size and material character. According to some embodiments, during a treatment, a thin layer of tissue grows the device (8) or a part thereof and encapsulates the device (8) or a part thereof, without a large amount of tissue encroaching the shunt lumen.

In some embodiments of the present teachings, the device in its delivery configuration is configured to be delivered and deployed through a 5 French-12 French catheter. As the device is being deployed, the shunt portion expands radially while contracts longitudinally. In some embodiments, for a deployed device, the length of the shunt portion of a deployed device ranges from about 30 to about 70% of the length of the device in the delivery profile. In some embodiments, the cross section of the elongated delivery profile of the device has a diameter ranges from about 1 mm to about 4 mm. And, the cross section of the shunt portion in the deployed configuration has a diameter from about 3 mm to about 12 mm, or from about 110% to about 300% of that of the shunt portion in the delivery profile. In some embodiments, the strut of the shunt portion has a width of about 0.005 inch to about 0.030 inch. In the delivery profile, the gap between the two adjacent portions of the strut is from about 0" to about 0.010", and, upon deployment, the gap between the two adjacent portions of the strut is up to about 0.075". According to some embodiments, the scaffold layer is disposed or folded between two adjacent struts when the shunt portion is in its elongated delivery profile. Upon being fully deployed, as the adjacent struts move away from each other, the cover extends without distorting its pore size and material character.

An embodiment of the device (8) of the present teachings has an elongated profile for delivering through a catheter system and an expanded profile for securing the device (8) across the septum. In some embodiments, the device (8) is configured to transition from the delivery profile to the deployed profile through self-expansion or mechanical actuations. In some embodiments, during a deployment, both the left and proximal flange portions (12, 16) of the frame (10) bend radially away from the longitudinal axis of the shunt portion (14) and two adjacent struts forming each flange segment move away from each other. In some embodiments, the scaffold layer is disposed or folded between two adjacent struts as the flange segments is in its elongated delivery profile. When the device is fully deployed, as the adjacent struts move away from one another, the cover extends without distorting its pore size and material character.

Although embodiments shown in FIGS. 2-5 includes the scaffold layers (40a, 40b) bonded to both side of the frame surface, one ordinarily skilled in the art would understand that, in other embodiments, scaffold layers can be applied to only one side of the frame or only a portion of the device. For example, a scaffold layer can bond to the inner luminal surface of the shunt portion of the device. It is known that living cells infiltrate a sufficiently porous covering material, such as ePTFE, and that microcapillaries may form within and across the barrier wall so that a living intima can form along the luminal surface. In some instances, for example, where a large aperture with a greater pressure differential between the two atria is present or created, placing the cover on the luminal surface (which faces the blood flow) may result in an advantageous lamellar flow of the blood—a flow without significant turbulence. Another advantage of using luminal cover can include the improved anchoring of the device within the aperture created by the interactions between the structure of the shunt portion of the device and the tissue wall surrounding the aperture. In other embodiments, placing a barrier material only on the abluminal surface of the shunt portion has some benefits to patients.

For example, contacting blood with a metal structure may result in local, limited thrombosis. Thus, covering the abluminal surface of the shunt portion of the device can limit thrombosis and enhance healings. One ordinarily skilled in the art would understand that optimal configurations of the cover will have to be determined by clinicians based on each patient's conditions. The specific embodiments discussed herein should not be viewed as limiting.

It is important to note that while the continuous tubular layer of cover is shown on the luminal surface of FIGS. 2a-2b and 5, it is possible, and advantageous in some cases, to place scaffold layer in sections. For example, scaffold layers can be placed in sections. The distances between these sections can be small or great, depending on the needs of a particular application. Moreover, the sizes, shapes, numbers and/or locations of the covered sections can vary and be determined by a clinician according to a patient's needs and the desired shape or strength of the shunt portion.

The methods and devices disclosed herein are useful for treating various symptoms of heart failures, in particular diastolic heart failures, by reducing the pressure in the left atrium and/or pulmonary veins. One ordinarily skilled in the art would further recognize that devices according to the present teachings can be used to regulate the pressures in other parts of the heart and/or vascular portions of the body. For example, the devices disclosed herein can be deployed on the septum between the left and right atria, the left and right ventricles, the left atrium and the coronary sinus, and the like.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein are for the purpose of description and should not be regarded as limiting.

We claim:

1. A device, having a first elongated profile and a second radially expanded profile, comprising a frame and a scaffold,
   wherein the frame comprises a first flange portion, a second flange portion, and a shunt portion;
   wherein the first flange portion comprises a plurality of flange segments, the second flange portion comprises a plurality of flange segments, wherein each flange segment of the first and second flange portions is made of two adjacent struts joining each other at their ends;
   the shunt portion has a generally tubular shape with a first end and a second end; wherein the flange segments of the first flange portion position side by side apart from one another and join the first end of the shunt portion along its entire circumference, and the flange segments of the second flange portion position side by side apart from one another and join the second end of the shunt portion along its entire circumference;
   wherein the scaffold comprises a first layer and a second layer, the first layer of the scaffold disposes against the first surface of the frame, the second layer of the scaffold disposes against the second surface of the frame, and the first and second layers of the scaffold are bonded to each other sealing around every strut that forms the frame of the device, and wherein the sealing between the first and second layers of the scaffold is biased toward one of the first or second layer leaving one exterior surface of the device even and an opposing exterior surface of the device uneven;
   wherein, when the device is in the second radially expanded profile, all flange segments of the first and second flange portions bend radially outward from the longitudinal axis of the shunt portion with the second flange portion bending toward the first flange portion for about 130° from the longitudinal axis of the shunt portion, and two adjacent struts of each flange segment of the first and second flange portions bow apart from each other and portions of the first and second layers of the scaffold are bonded between the two adjacent struts;
   and wherein the scaffold is configured to allow the device to transform from the first elongated profile to the second radially expanded profile without introducing any stress to the frame.

2. The device of claim 1, wherein the first flange portion bends for about 90° outward from the longitudinal axis of the shunt portion as the device is in the second radially expanded profile.

3. The device of claim 1, wherein the scaffold is made of a nitinol mesh.

4. The device of claim 1, wherein the flange segments of the first and second flange portions align parallelly to the longitudinal axis of the shunt portion when the device is in its first elongated profile.

5. The device of claim 1, wherein the first layer of the scaffold comprises pores with a first pore size and the second layer of the scaffold comprises pores with a second pore size.

6. The device of claim 5, wherein the first and second pore sizes are different.

7. The device of claim 1, wherein at least one of the first and second layers of the scaffold is made of multiple members of different shapes for covering the first and second flange portions and shunt portion.

8. The device of claim 7, wherein at least one member of the scaffold comprises a pore size different than those of another member of the scaffold.

9. The device of claim 1, wherein a distal tip of the first and second flange portions include a through hole to allow the scaffold on both sides of the frame to meet and bond.

10. A device, having a first elongated profile and a second radially expanded profile, comprising a frame and a scaffold,
    wherein the frame comprises a first flange portion, a second flange portion, and a shunt portion;
    wherein the first flange portion comprises a plurality of flange segments, wherein each flange segment of the first flange portions is made of two adjacent struts joining each other at their ends; the second flange portion comprises a plurality of flange segments, wherein each flange segment of the second flange portions is made of two adjacent struts joining each other at one ends;
    the shunt portion has a generally tubular shape with a first end and a second end; wherein the flange segments of the first flange portion position side by side apart from one another and join the first end of the shunt portion along its entire circumference, and the flange segments of the second flange portion position side by side apart from one another and join the second end of the shunt portion along its entire circumference;
    wherein the scaffold comprises a first layer and a second layer, the first layer of the scaffold disposes against the first surface of the frame, the second layer of the scaffold disposes against the second surface of the frame, and the first and second layers of the scaffold are bonded to each other sealing around every strut that forms the frame of the device, and wherein the sealing between the first and second layers of the scaffold is biased toward one of the first or second layer leaving one exterior surface of the device even and an opposing exterior surface of the device uneven;

wherein, when the device is in the second radially expanded profile, two adjacent struts of each flange segment of the first and second flange portions bow apart from each other with portions of the first and second layer of the scaffold are bonded between the two adjacent struts;

wherein, when the device is in the first radially expanded profile, the scaffold between the two adjacent struts is folded inward along the longitudinal axis of the shunt portion; and a pore size of the scaffold maintains substantially the same when the device is in the first elongated profile and the second radially expanded profile; and wherein the scaffold is configured to allow the device to transform from the first elongated profile to the second radially expanded profile without introducing any stress to the frame.

11. The device of claim 10, wherein the device in its first elongated profile fits inside a 5 French-12 French catheter.

12. The device of claim 10, wherein the shunt portion expands at least 100% in its diameter when the device transitions from the first elongated profile to the second radially expanded profile.

13. The device of claim 10, wherein the flange segments of the first and second flange portions bend radially away from the longitudinal axis of the shunt portion with the second flange portion bending toward the first flange portion for about 130° from the longitudinal axis of the shunt portion as the device transitions from the first elongated profile to the second radially expanded profile.

14. The device of claim 10, wherein the scaffold is made of a nitinol mesh.

\* \* \* \* \*